US010521553B2

(12) United States Patent
Serra del Molino et al.

(10) Patent No.: US 10,521,553 B2
(45) Date of Patent: Dec. 31, 2019

(54) METHOD, SYSTEM AND COMPUTER PROGRAM FOR DETERMINING THE POROSITY OF A FLEXIBLE POROUS STRUCTURE SUBJECTED TO DEFORMATION

(71) Applicant: GALGO MEDICAL, S.L., Barcelona (ES)

(72) Inventors: Luis Serra del Molino, Barcelona (ES); Ignacio Larrabide Fernandez, Tandil (AR); Héctor Fernandez Martinez, Barcelona (ES)

(73) Assignee: GALGO MEDICAL, S.L., Barcelona (ES)

( * ) Notice: Subject to any disclaimer, the term of this patent is extended or adjusted under 35 U.S.C. 154(b) by 273 days.

(21) Appl. No.: 15/545,902

(22) PCT Filed: Jan. 25, 2016

(86) PCT No.: PCT/IB2016/000043
§ 371 (c)(1),
(2) Date: Jul. 24, 2017

(87) PCT Pub. No.: WO2016/120704
PCT Pub. Date: Aug. 4, 2016

(65) Prior Publication Data
US 2018/0336310 A1 Nov. 22, 2018

(30) Foreign Application Priority Data

Jan. 26, 2015 (ES) .................................. 201530096

(51) Int. Cl.
*G06F 11/30* (2006.01)
*G06F 19/00* (2018.01)
(52) U.S. Cl.
CPC .................................. *G06F 19/00* (2013.01)

(58) Field of Classification Search
CPC ...................................................... G06F 19/00
See application file for complete search history.

(56) References Cited

U.S. PATENT DOCUMENTS

| | | | |
|---|---|---|---|
| 6,010,468 A | | 1/2000 | Grove et al. |
| 6,083,257 A | * | 7/2000 | Taylor ........................ A61F 2/90 |
| | | | 623/1.46 |
| 2007/0135707 A1 | | 6/2007 | Redel et al. |

FOREIGN PATENT DOCUMENTS

| | | |
|---|---|---|
| ES | 2459244 | 11/2014 |
| WO | 2006093776 | 9/2006 |
| WO | 2011038044 | 3/2011 |

OTHER PUBLICATIONS

Dierick M. et al.: "The use of 2D pixel detectors in micro-and nano-CT applications", vol. 591 No. 1 Jun. 11, 2008 chapter 3.3. Figure 3 (Year: 2008).*

(Continued)

*Primary Examiner* — Phuong Huynh
(74) *Attorney, Agent, or Firm* — Silvia Salvadori

(57) ABSTRACT

A method, system and computer program are provided for determining the porosity of a flexible porous structure when it is subjected to deformation. The method performs the following steps by processing representative data of the flexible porous structure: a) generates a first function ($F_s$) defining how the flexible porous structure changes shape when it is subjected to deformation; b) generates a second function ($F_p$) defining how a covered surface of the flexible porous structure changes when it is subjected to changes in shape, wherein the second function ($F_p$) is directly linked with porosity of the flexible porous structure; c) obtains reference porosity values of a reference region (CU-R) of the flexible porous structure in a reference configuration via the first function ($F_s$); and d) calculates the porosity of at least one deformed region (CU-D) of the flexible porous (Continued)

structure, from said reference porosity values and from the second function ($F_p$).

20 Claims, 2 Drawing Sheets

(56) References Cited

OTHER PUBLICATIONS

Minsuok Kim et al.: "Comparison of Two Stents in Modifying Cerebral Aneuysm Hemodynamics", vol. 36, No. 5 Feb. 9, 2008 Figures 1-19 (Year: 2008).*
Dierick M. et al.: "The use of 2D pixel detectors in micro- and nano-CT applications". vol. 591 No. 1 Jun. 11, 2008 chapter 3.3. figure 3.
Minsuok Kim et al.: "Comparison of Two Stents in Modifying Cerebral Aneurysm Hemodynamics". vol. 36, No. 5 Feb. 9, 2008 figures 1-19.
A Makoyeva et al.: "The Varying Porosity of Braided Self-Expanding Stents and Flow diverters: An Experimental Study".vol. 34, No. 3 Aug. 9, 2012 figures 1-7.
Cebral J R et al: "Efficient Simulation of Blood Flow Past Complex Endovascular Devices Using and Adaptive Embedding Technique". vol. 24, No. 4 Apr. 1, 2005 figures 1-15.
Ignacio Larrabide et al.: "Fast virtual deployment of self-expandable stents: Method and in vitro evaluation for Intracranial aneurysmal stenting".vol. 16 No. 3, May 11, 2010.
William E Lorensen et al.: "Marching cubes: A High resolution 3D surface construction algorithm".vol. 21, No. 4 Jul. 1, 1987.
Ding Ma et al. "Computer modeling of deployment and mechanical expansion of neurovascular flow diverter in patient-specific intracranial aneurysms". vol. 45 No. 13 Aug. 1, 2012.
Fabrice Bing et al.: "Stents and flow diverters in the treatment of aneurysms: device deformation in vivo may alter porosity and impact efficacy"vol. 55, No. 1 Aug. 16, 2012.
International Search Report and written opinion of PCT/IB2016/000043 dated Jun. 30, 2016.

* cited by examiner

METHOD, SYSTEM AND COMPUTER PROGRAM FOR DETERMINING THE POROSITY OF A FLEXIBLE POROUS STRUCTURE SUBJECTED TO DEFORMATION

RELATED APPLICATIONS

This application is the US national phase application of international application number PCT/IB2016/000043, filed 25 Jan. 2016, which designates the US and claims priority to Spanish application ES P 201530096.1 filed 26 Jan. 2015, the contents of each of which are hereby incorporated by reference as if set forth in their entireties.

TECHNICAL FIELD

In a first aspect, the present invention relates to a method for determining the porosity of a flexible porous structure when it is subjected to deformation by means of processing representative data of the flexible porous structure.

In a second aspect, the present invention relates to a system for determining the porosity of a flexible porous structure when it is subjected to deformation by means of implementing an algorithm carrying out the steps of the method of the first aspect of the invention.

A third aspect of the invention relates to a computer program implementing the steps of the method of the first aspect of the invention.

In a non-limiting manner, the present invention is particularly applicable to determining porosity of a tubular-shaped flexible porous structure, especially of a stent.

BACKGROUND ART

Generally, the term stent is a commonly used medical term to refer to a cannula or cylindrical- or tubular-shaped device for endoluminal, usually endovascular, use which is placed inside an anatomical structure or a duct in the body in order to keep it permeable or to prevent its collapse after surgical release, dilation, or clearance. A stent is usually implanted in a blood vessel at the site of an endoluminal aneurysm or stenosis, i.e., by means of so-called "minimally invasive techniques", in which the stent is contained in a configuration that is radially compressed by a tube or catheter and is delivered by means of a stent applicator or "introducer" in required location. The introducer can enter the body from an access site outside said body, such as through the skin of the patient, or by means of a sectioning technique in which the incoming blood vessel is exposed to minor surgical procedures.

As it is used herein, the term stent also refers to grafts, stent grafts, vein cava filters, expanding structures and similar implantable medical devices, which are radially expanding endoprotheses. They are normally are intravascular implants that can be transluminally implanted and they radially enlarge after having been introduced percutaneously.

Stents can be implanted in various cavities or vessels in the body, such as in the vascular system, the urinary tract, bile ducts, among others. Said stents can be used to reinforce blood vessels and to prevent re-stenosis followed by angioplasty in the vascular system. Stents can be self-expanding, such as nitinol shape memory stents; furthermore, mechanically expanding, such as an expanding balloon stent; or expanding hybrid stents.

The use of endoluminal stents is very common in different areas of medicine and veterinary science. There are different stent designs for endoluminal insertion in blood vessels and other lumina to prevent or reverse the blocking thereof.

It is generally considered that there are three basic categories of stent type devices, namely:
heat-expandable devices,
expanding balloon devices, and
self-expanding devices.

Self-expanding type stent devices, which can optionally be heat-expandable, are inserted in a vessel in the body in radially compressed form and mechanically transition to a radially expanded position. Once the stent is placed in the desired position in the blood vessel, it expands radially, applying outward pressure on the inner surface of the wall of the vessel in the body in which it has been placed.

In turn, there are braided stents and unbraided stents. Braided stents are made by braiding (interweaving) wires of a fine metallic material according to different braiding patterns. Patent document U.S. Pat. No. 6,083,257A discloses a methodology for braiding stents. Depending on the number of wires, the braiding angle, the nominal radius, the nominal length and the braiding pattern used, the mechanical properties and density of the resulting stent mesh can vary considerably.

Stents are often used for treating intracranial aneurysms (IA), a sector where there are different types of braided stents. One of those types is known as a "flow diverter" (FD), which is densely braided and placed longitudinally along the vessel affected by the aneurysm and covers the neck of the aneurysm. Alternatively, thickly braided stents are also used as a scaffold for protecting the neck of the IA after placing an endovascular coil, as disclosed in patent document U.S. Pat. No. 6,010,468A.

Stents are placed in the desired site by means of a catheter in image-guided operations, conventionally with X-ray image guiding, the interventionalist with the aid of a contrast agent that highlights the location of the lumen of the vessel and, where appropriate, of the aneurysm to be treated. In the case of aneurysms, the catheter is inserted in the body normally through arteries, for example the iliac artery, and is led to the location of the aneurysm by a neurointerventional radiologist. Said radiologist will select the position in which the distal side of the stent is placed and will progressively take the stent out of its sheathe until it is completely released in the treated vessel.

Stents have the difficulty that the final porosity of the stent is not known a priori when it is placed inside the body and the value of which determines both the amount of flow entering the aneurysm to be treated and the vessels adjacent that are covered by the stent.

Porosity of a stent when it is placed inside a vessel can be approximated assuming that the stent is released in a straight vessel having a constant radius. This calculation consists of determining the area of the outer wall of the cylinder generating the stent, based on its radius and length, and the surface area of metal covering said cylinder, based on the number of wires, the thickness of each wire, its length and the number of cross points between wires on the surface of the stent. This method provides rather imprecise approximations of the porosity the stent will have once it is inserted in the patient's vasculature given that vessels are generally heterogeneous tubular structures both in terms of radius and in terms of their three-dimensional morphology, having curvatures and twisting.

When a stent is located outside of a structure delimiting it, such as a vessel, as previously mentioned, it adopts its maximum radius and minimum length in the absence of stresses. However, if said stent is placed inside a vessel having a radius smaller than the radius it has outside a structure delimiting it, the walls of the vessel delimit the radial expansion of the stent, forcing the device to expand longitudinally until achieving a balance situation. This makes the stent in the vessel have a longer length than it does in the air. This, added to the fact that it is deployed in a curved tubular structure, causes porosity to depend on the point of the surface of the stent on which said porosity is measured. Therefore, measuring porosity of said device before placement thereof does not provide realistic values about the behavior of the stent once it is inserted. The interventionalist does not have tools for estimating, a priori, porosity of the stent once it is placed inside the patient. In the case of intracranial aneurysms, the variation in the density of the stent mesh as a result of the different degrees of expansion and curvature to which the stent is subjected means that the effect of the device on blood flow inside the aneurysm is difficult to predict. For this reason, there is a need to provide a tool that allows precisely predicting the final porosity of a stent once it is placed inside the body.

There are background documents describing methods for modeling stents. Deformable models have been used to simulate the behavior of a stent when it is placed inside the lumen of a vessel (Larrabide, I. et al. "Fast virtual deployment of self-expandable stents: method and in vitro evaluation for intracranial aneurysmal stenting." Medical image analysis, 2012, 16(3), 721-730). However, said method does not allow predicting porosity of the stent, given that it does not take into account its longitudinal deformation.

Other methods based on the mechanical deformation of a cylinder-like structure have also been proposed (Cebral, J. R. and Lohner, R. "Efficient simulation of blood flow past complex endovascular devices using adaptive embedding technique." IEEE Transactions on Medical Imaging, 2005, 24(4), 468-476), but they are not able to predict the change in porosity of the stent either.

A method based on the use of finite elements and a detailed description of the braiding pattern, which allows a more precise modeling of the mechanical behavior of the stent type device, has recently been disclosed (Ma, D. et al. "Computer modelling of deployment and mechanical expansion of neurovascular flow diverter in patient-specific intracranial aneurysms." Journal of biomechanics, 2012, 1-8). This method is considerably precise when modeling the behavior of a stent, but obtaining the models is extremely complex and computationally expensive.

Other methods based on obtaining images of the lumina of the vessels to be treated and modeling for determining the most suitable stent are those disclosed in international patent applications WO2006/093776 and WO2011/038044, and in US patent application US2007/0135707, although none of them describes use thereof for determining the porosity of the stent.

International patent application WO2006/093776 discloses a method of modeling stents based on using an ultrasonic imaging system for obtaining images of blood vessels, detecting defects in said vessels and using said images to perform graphic simulations with different stents to check if the length and position are suitable.

International patent application WO2011/038044, in turn, discloses an automated method for simulating the length and position of stents based on obtaining images of the lumen of the blood vessel by means of optical coherence tomography. A three-dimensional reconstruction of the contours of the lumen of the vessel is performed from the images obtained, data relating to the diameter of the vessel and to the blood flow rate, pressure and resistance is obtained to finally simulate and optimize the length and/or position of the stent.

Finally, US patent application US2007/0135707 discloses obtaining three-dimensional images used to build a model of the vessel to be treated to detect the lesion and its characteristics and to simulate the stent to be used and the position in which it will be placed.

The authors of the present invention do not know of any method or system that allows determining porosity of a stent or of any other class of flexible porous structure, whether tubular or not, when it is subjected to deformation, by means of processing representative data of the flexible porous structure, i.e., without being able to directly check on the flexible porous structure the porosity that it has, for example, since the porous structure is placed in an inaccessible site, as is the case of a stent implanted inside the human body.

There is a need, therefore, to provide a solution to the objective technical problem relating to how to determine porosity of a flexible porous structure when it is subjected to deformation by means of processing representative data thereof.

DESCRIPTION OF THE INVENTION

The present invention constitutes, in its different aspects, such solution to the aforementioned objective technical problem.

In a first aspect, the present invention relates to a method for determining the porosity of a flexible porous structure when it is subjected to deformation, which comprises performing the following steps by means of processing representative data of said flexible porous structure:

a) generating a first function ($F_s$) defining how at least one part of the flexible porous structure, given its coordinates, changes shape when it is subjected to one or more geometric deformations;

b) generating a second function ($F_p$) defining how a covered surface, and/or a variable associated with same, for at least one part of the flexible porous structure, changes when it is subjected to one or more changes in shape;

c) obtaining by means of said first function ($F_s$) reference porosity values of at least one reference region (hereinafter referred to as CU-R or reference unit cell) of the flexible porous structure in a reference configuration; and d) calculating the porosity of at least one deformed region (hereinafter referred to as CU-D or deformed unit cell) of the flexible porous structure corresponding with said reference region but for a deformed configuration different from said reference configuration, from said reference porosity values and from at least said second function ($F_p$).

It must be indicated that the second function ($F_p$) is a function of the change in covered area of the flexible porous structure, which is linked directly with porosity.

The mentioned data to be processed form respective three-dimensional representations of the flexible porous structure for each of the configurations: the reference configuration and the deformed configuration.

Generally, the deformed region has experienced deformations with respect to the reference region in one or more dimensions.

In relation to the mentioned variable associated with porosity, depending on the embodiment, said porosity is relative to the occupancy of the material forming the flexible porous structure or to the degree of interstitial space, or free space of the material forming the flexible porous structure.

For a preferred embodiment, the method proposed by the first aspect of the present invention comprises:

x1) selecting, before step c), at least said deformed region CU-D of the flexible porous structure in said deformed configuration; and x2) calculating, after step c), the shape of at least said reference region CU-R of the flexible porous structure using said first function $F_s$, using the coordinates corresponding to the deformed region CU-D.

Preferably, the first function $F_s$ defines how said part of the flexible porous structure changes shape in one or more of its dimensions affecting porosity.

In relation to the calculation of step x2), a possible change in spatial position of region CU-R with respect to CU-D is generally not taken into account in that calculation, although the method of the present invention also contemplates, for another embodiment, taking such change in spatial position into account, if it were to occur, in the calculation of step x2).

According to One Embodiment:

the second function $F_p$ generated in step b) defines how the occupancy of the material forming the flexible porous structure changes for at least said part of the flexible porous structure;

after step x2) and prior to the calculation of porosity of the flexible porous structure in the deformed region (CU-D) of step d), the method comprises calculating the occupancy of the material forming the flexible porous structure for at least said reference region CU-R, from said reference porosity values; and step d) comprises:

d1) calculating the occupancy of the material forming the flexible porous structure for at least said deformed region CU-D using the second function $F_p$ and the calculated occupancy of the reference region CU-R; and d2) calculating the porosity in the deformed region CU-D from said occupancy of same calculated in d1) and from its total dimension.

According to a variant of said embodiment, step d2) comprises calculating the degree of interstitial space, or free space of the material forming the flexible porous structure, from said occupancy, and carrying out said calculation of porosity from said degree of interstitial space by calculating the quotient between interstitial space and total space of the deformed region CU-D.

Generally, both the parts of the flexible porous structure of steps a) and b) and the deformed region CU-D and reference region CU-R are area elements on a perimetral surface of the flexible porous structure (i.e., a surface demarcated by two planes having a parallel section of the flexible porous structure), although less preferably, volume elements can be used instead of area elements.

Preferably, the flexible porous structure is tubular, such as a stent or any other class of flexible porous tubular structure, such as, for example, a porous structure inserted or a porous structure covering a conduit or tube installed in a hard-to-access location or in a location with very restricted access, as in the case, for example, of a contaminating or toxic area, such as a radioactive area (such as in a nuclear facility).

Nevertheless, it must be highlighted that the present invention is not limited to any class of flexible porous structure in particular, but rather covers any flexible porous structure, whether tubular or non-tubular (for example a WEB® aneurysm embolization system), of any shape and composition which, for whatever reason, does not allow or makes it unadvisable to determine its porosity by means of direct visual inspection, for which purpose said porosity must be determined based on processing representative data thereof. Such reasons are, for example, those mentioned above, i.e., the structure is implanted in the human body or located in a contaminating or toxic area, or an area of another type, such as the case of micrometric-sized structures the inspection of which, even by means of microscopy techniques, is difficult when they are subjected to deformation.

For the case in which the flexible porous structure is a stent, said stent is generally of the previously mentioned self-expanding stent type devices which, optionally, have heat-expansion capacity, which are inserted in a vessel inside the body in radially compressed form and mechanically transition to a radially expanded position.

The present invention is applicable to both braided stents and to non-braided stents, provided that the stent changes in porosity when the spatial configuration thereof changes.

Generally, for the case in which the flexible porous structure is tubular, the mentioned perimetral surface is the perimetral outer surface of the flexible porous tubular structure.

The mentioned first function $F_s$ defines, according to a preferred embodiment, how the surface of the flexible porous structure changes shape when it is subjected to one or more geometric deformations, i.e., starting from CU-D, giving rise to CU-R.

In relation to the second function $F_p$, according to a preferred embodiment said function defines how the covered surface and/or the mentioned variable associated with same for a surface element of the flexible porous structure, changes when it is subjected to one or more changes in shape, i.e., starting from the covered surface in CU-R giving rise to the covered surface in CU-D.

Preferably, the method proposed by the first aspect of the invention comprises performing steps x1), x2) and said calculation of porosity of the deformed region (CU-D) of the flexible porous structure for several deformed regions CU-D of the flexible porous structure and the corresponding reference regions CU-R, where the deformed regions CU-D preferably are not superimposed on one another.

According to one embodiment, the deformed regions CU-D completely occupy the perimetral surface of the flexible porous structure, where the method comprises dividing the perimetral surface into said deformed regions CU-D prior to step x1).

The method proposed by the first aspect of the present invention comprises processing the several porosity values obtained in the corresponding steps d) to perform one or more of the following actions, according to several embodiments:

determining the spatial distribution of porosity throughout the flexible porous structure;

obtaining a porosity value combining at least several of said porosity values for a zone of the flexible porous structure that includes several deformed regions CU-D; and visually representing on a three-dimensional model of the flexible porous structure the spatial distribution of porosity for individual deformed regions CU-D and/or groups of deformed regions CU-D.

According to one embodiment, the reference configuration corresponds to a situation in which the flexible porous structure is released into a medium in which it is not subject to external stresses deforming it.

For an alternative embodiment, the reference configuration corresponds to a situation in which the flexible porous structure is deformed but with a reference deformation that is different from that of the deformed configuration.

For the case in which the flexible porous structure is tubular, according to a variant of said alternative embodiment the mentioned reference deformation is a deformation that keeps the flexible porous tubular structure straight and with a uniform radius along its entire length.

Reference deformations of another class are also possible for other embodiments, such as reference deformations making the flexible porous structure adopt a curved shape, such as a toroid.

In relation to the deformed configuration, according to one embodiment, for such deformed configuration the flexible porous structure adopts a heterogeneous radius and a heterogeneous three-dimensional morphology, where said heterogeneous three-dimensional morphology includes at least one curvature and/or at least one twist.

According to one embodiment, in said deformed configuration the flexible porous structure adopts a conical shape.

According to one embodiment, the data making up the previously mentioned three-dimensional representations are obtained by means of simulation.

Alternatively, the data making up the three-dimensional representations are obtained directly on a real flexible porous structure placed covering an outer surface of a solid or hollow element, or an inner surface demarcating a hollow part of an element. When such element is a tube (such as a blood vessel), the mentioned hollow part is the part demarcated by the inner wall of the tube, the flexible porous structure, in this case tubular, being able to be arranged covering said tube or placed against the inner wall thereof.

According to one embodiment, the method comprises carrying out the calculation of porosity for several deformed spatial configurations, with different deformations, corresponding to several respective positions adopted by means of the flexible porous structure in said simulation or in relation to said element.

Generally, the reference porosity values of the reference region CU-R are known (for example provided by the manufacturer of the flexible porous structure) and are recorded in the memory, where the method comprises performing said obtaining of said reference porosity values of said reference region CU-R by accessing same in said memory. For the more usual case in which porosity of the flexible porous structure is uniform for the entire structure, the mentioned reference porosity values are relative to the entire structure, not only to said reference region CU-R.

For the case in which such reference porosity values are not known in principle, the mentioned obtaining of same is carried out by determining them by any method known, such as from direct visual inspection of the flexible porous structure in its reference position.

In a preferred embodiment, the method of the present invention is used in the medical or veterinary field for predicting the porosity of stents when said stents are placed inside living bodies.

The method of the present invention can be carried out with the help of one or several computer programs, i.e., as a computer-implemented method.

In a second aspect, the present invention relates to a system for determining the porosity of a flexible porous structure when it is subjected to deformation, comprising data processing means with access to reference porosity values of at least one reference region CU-R of the flexible porous structure in a reference configuration, and which implement an algorithm for processing representative data of said flexible porous structure for the calculation of porosity according to the method of the first aspect.

A third aspect of the present invention relates to a computer program including code instructions which implement the steps of the method of the first aspect when they are run in a computer.

According to one embodiment, the system comprises:
computing means including said processing means; and
display means (such as a screen) configured for, under the control of said computing means, showing a three-dimensional representation of the flexible porous structure for the deformed configuration with the spatial distribution of porosity calculated for individual deformed regions CU-D and/or groups of deformed regions CU-D.

For one embodiment, the computing means are configured for carrying out said calculation of porosity for several deformed configurations, with different deformations, corresponding to several respective positions adopted by the flexible porous structure, and for controlling the display means so that they show a three-dimensional representation of the flexible porous structure for said deformed configurations with their respective spatial distributions of porosity for individual deformed regions CU-D and/or groups of deformed regions CU-D. It is thereby allowed that, for the case in which the flexible porous structure is a stent, prior to being implanted in, for example, a blood vessel, the surgeon can check how the distribution of porosity changes for different positions of the stent in relation to the blood vessel, in order to thus choose the most suitable one for the implant.

In the present document, the terms "vascular structure", "vessel" and "vessels" refer to arteries, arterioles, veins, intestine, rectum and any other tubular type structure present in the human or animal body, which is susceptible to being treated with stents. In the present document, the terms "stent" and "stent type device" refer to braided stents, non-braided stents and equivalents. Furthermore, the present invention covers both stents of constant radius (cylindrical) and stents of non-constant radius (conical, conical/cylindrical combinations, among others).

For a homogenous expansion of a braided stent, it is possible to relate the interweaving angle for different radii of expansion with the porosity of the stent, which in this situation will be constant on the entire surface thereof. This allows for experimental validation of the method proposed by the present invention.

Once the final porosity of the stent is obtained for each position, said porosity can be represented on the three-dimensional representation of the stent by means of a color code (or another class of code) associated with the range of porosity values between 0 and 1. Said color code can be obtained by any of the methods known in the state of the art.

An additional advantage of the method of the present invention is that it allows identifying the regions in which the stent has null porosity, blocking circulation through the stent mesh. Such regions can present risks for the patient such as, in the case of blood flow diverters, the lack of irrigation to regions affected by collateral branches.

BRIEF DESCRIPTION OF THE DRAWINGS

The preceding and other advantages and features will be better understood from the following detailed description of embodiments with reference to the attached drawings, which must be interpreted in an illustrative and non-limiting manner, in which.

DETAILED DESCRIPTION OF EMBODIMENTS

Figure 1:
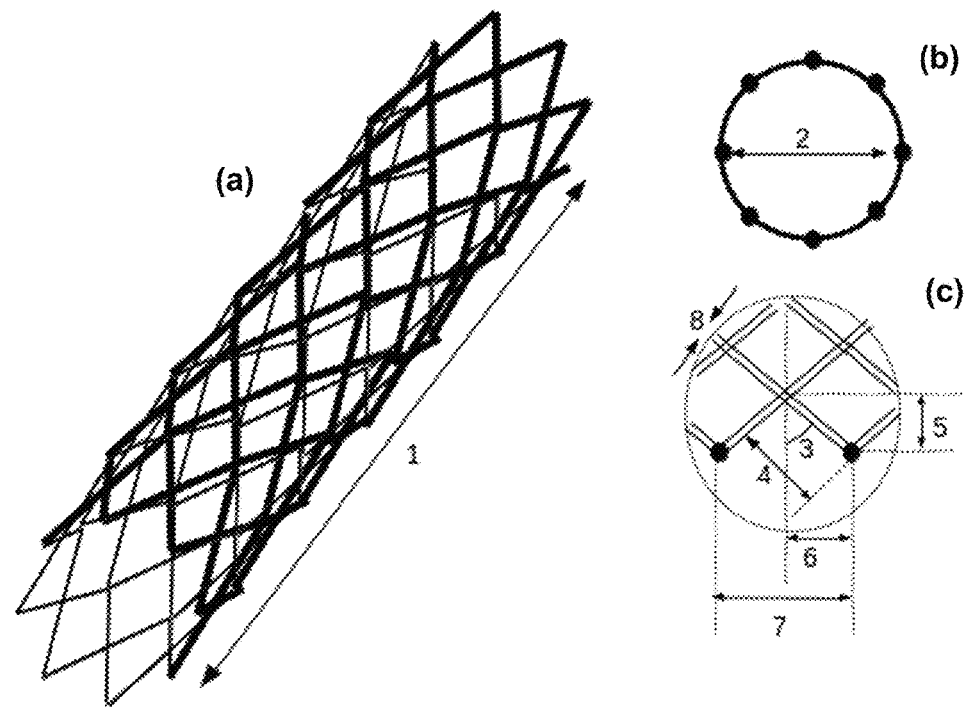
FIG. 1 shows a perspective view of a stent released in the air adopting a tubular structure (a), as well as a cross-section view thereof (b) and a detail of the interweaving (c).

As described up until now, the authors of the present invention have developed a method for determining the porosity and distribution thereof for a flexible porous structure. Said method allows determining in a very accurate manner the final porosity and the spatial distribution and variation thereof for a stent based on deformation with respect to a reference position or configuration.

In the present section, the term "reference radius" refers to the radius adopted by the stent in a reference configuration and expressed as a function of any of the design variables, or another feature of the stent, in said reference configuration, and the term "reference length" refers to the length adopted by the stent in the reference position. Therefore, the stent adopts the "reference length" when it has its "reference radius".

This section will focus on the description of the method for the case in which the flexible porous structure is a stent placed or to be placed in a vascular structure, and the CU-R and CU-D regions are area elements, the term CU-D being used to refer to any element on the surface of the stent once it is implanted, and the term CU-R being used to refer to the element equivalent to CU-D in the reference position or configuration.

In the present section, each of the different angles the wires of the stent have with respect to the longitudinal direction thereof is referred to as interweaving angle, the surface covered by the wires of the stent is referred to as occupied area, the surface not covered by the wires of the stent is referred to as free area, and the relation between the ratio of free area for a total given area on the surface of the stent is referred to as porosity.

As described in a previous section, the method of the present invention is based on the analysis of local deformation of the structure of the stent once it is placed. This calculation requires defining a relation of the change in area of the stent as a function of the change in its geometric configuration, which relation is defined by the aforementioned function $F_s$. It is also necessary to define a function that describes in what way the occupied area (or directly the porosity) is modified on the surface of the stent when said surface is deformed, which is carried out by means of the function $F_p$, described in a preceding section.

The function determining the change in total area of the stent with the variations in its geometry is determined in two directions defining that transformation between surfaces, i.e.: $F_s = F_{s1} * F_{s2}$.

On one hand, in the cross-section of the stent, $F_{s1}$, the change in total area of the stent is defined by the change in its perimeter due to radial expansion. For deformations of the stent without circular symmetry, the transformation is defined by the ratio between the arc length in the reference position and the arc length once the stent is adapted to the surface in which it is deployed.

On the other hand, in the longitudinal direction, $F_{s2}$, the change in area is determined by the change in length of the stent when it expands in the tubular structure delimiting it. This function can be determined with different methodologies. One way, with a constant value along the entire stent, is to define this function as the ratio between the length in the measurement position and the length in the reference position. Another way can be by considering the different degrees of expansion the stent experiences as a function of its position in the vessel, as described in detail in patent document ES2459244B1. The greater the degree of detail used to define this function, the greater the approximation that is obtained in the result with respect to the real case.

The function defining the change in occupied area with respect to deformations on the surface of the stent, $F_p$, can be defined by several methods. This function can be determined empirically by measuring the area of the stent and the amount of visible wire when the device is deployed in various straight cylinders of variable radius. In an analytical manner, it can be defined by calculating the variation in the occupied area in the stent. For this purpose, a distribution for the wires on the surface is assumed and for said distribution, it is calculated how the overlapping surface changes between pairs of wires given different stent diameters. In each case, the occupied surface in the stent is the surface occupied by each wire multiplied by the number of wires minus the overlapping wire surface at the cross points. Another way to extract this function in an analytical manner is to define an area element in the stent such that, under rigid transformations of this element, the surface of the stent can be covered. The calculation of the function of the change in occupied area is determined by deforming the surface element and determining how its occupied area is adapted to the new configuration.

Once the functions $F_s$ and $F_p$ are determined, according to one embodiment the method of the present invention for determining the porosity of a stent when it is placed in a 3D structure comprises the following steps:

E1. Obtaining a tubular representation of the stent in the reference position (20 in FIG. 4) with known porosity, or reference porosity, values.

E2. Obtaining a tubular representation of the stent in its deployed position object of study (21 in FIG. 4).

E3. Dividing the surface of the stent into a set of area elements CU-D such that they cover the entire surface thereof and preferably do not overlap one another (CU-D: element 23 in FIG. 4).

E4. Calculating CU-R (22 in FIG. 4), i.e., its shape, in the reference configuration R by means of using $F_s$ (step 24 in FIG. 4), where CU-R is equivalent to CU-D.

E5. Calculating the covered area in the element CU-R given the reference porosity in the position CU-R.

E6. Calculating the covered area in CU-D from the function $F_p$ relating the covered areas in CU-D and CU-R (step 25 in FIG. 4).

E7. Calculating porosity in the element CU-D as the quotient between the non-covered area and the total area of CU-D;

E8. Repeating the step 4), 5), 6) and 7) for all the CU-Ds.

For another embodiment, some of the preceding steps can be omitted, as described in a preceding section, particularly when for the calculation of porosity it is not necessary to first determine the occupied area. Specifically, for such embodiment, the function $F_p$ defines how porosity of the flexible porous structure changes, and therefore steps E5 and E6 are not necessary and are replaced with a single step that comprises calculating the porosity of CU-D directly using the function $F_p$ and the reference porosity values of CU-R.

FIGS. 1 to 4 show different representations of the stent and of parts thereof, in a more or less schematic manner.

Particularly, FIG. 1 shows a perspective view of the stent (a), formed by a series of interwoven wires, a cross-section view of the stent (b) and an enlarged portion thereof with a detail of the interweaving of the wires of the stent (c). The length of the stent -1-, the diameter -2-, the braiding angle -3-, the length between two cross points of the stent -4-, the longitudinal and transverse projection, along the perimeter, of the distance between cross points -5- and -6-, the distance between cross points along the perimeter -7- and the thickness of the wire -8- are shown in detail in said FIG. 1.

Figure 2:
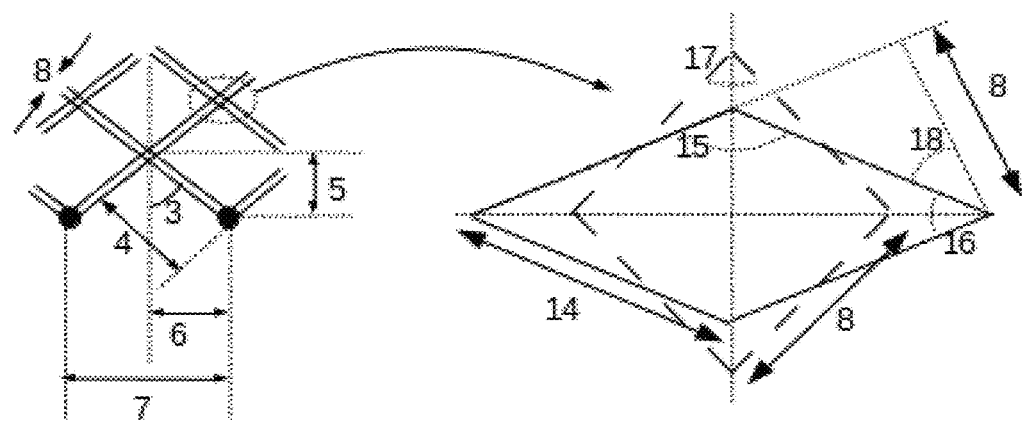
FIG. 2 shows, on the left, the detail of view (c) of FIG. 1, and, on the right, an enlarged view of part of same corresponding to the cross point between two wires of the stent, in which the difference of covered area in two cross point positions is observed.

The detailed view (c) of FIG. 1 is also depicted in FIG. 2 (view on the left) together with an enlargement thereof (view on the right) illustrating the cross point between two wires and how the area thereof changes when the stent is subjected to deformation. The figure shows in detail: braiding angle -3-, length between two cross points of the stent -4-, longitudinal and transverse projection, along the perimeter, of the distance between cross points -5- and -6-, distance between cross points along the perimeter -7- and thickness of the wire -8-, the crossing angle when the wires are perpendicular -17-, the crossing angles for an arbitrary position -15 and -16- (and the complementary angle thereof -18-), as well as the length of the overlap zone for an arbitrary position -14-.

Figure 3:
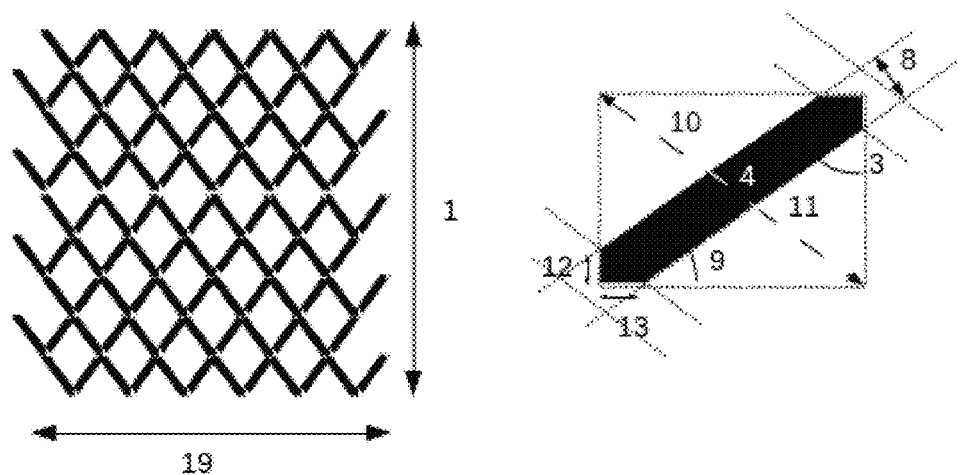
FIG. 3 shows, on the left, the development of a stent cut along the length thereof and extended on a plane and, on the right, a detail of the structure and the area occupied by a wire element connecting two cross points.

The development of a stent like that shown in FIG. 1 is illustrated in the view on the left of FIG. 3, which, on the right, shows a detail of the structure and the area occupied by a wire element connecting two cross points of the stent. Said figure shows in detail the length of the stent -1-, the length of the perimeter -19-, the thickness of the wire -8-, the crossing angles, along the braiding, and the complementary angle thereof, -3- and -9-, the areas not occupied by metal -10- and -11-, two dimensions indicative of the measurements of the wire -12- and -13- and the length of wire between two cross points -4-.

Figure 4:
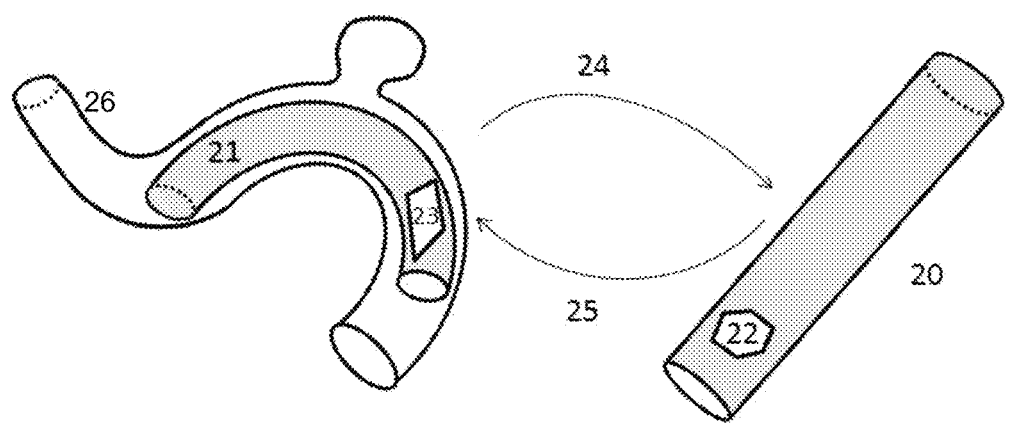
FIG. 4 corresponds to a detail of a stent in a deformed configuration when it is implanted in a vessel in the body, on the left, and of the same stent deployed in a reference position or configuration, on the right.

Finally, and in a more schematic manner (because the wires of the stent are not illustrated), FIG. 4 illustrates, in the view on the left, the stent inserted in a vessel -26- in the body, adopting a deformed configuration -21-, and in the view on the right, it illustrates the stent in a reference configuration -20- in which, in this case, the stent is deployed adopting a cylindrical shape. The figure shows a deformed region CU-D of a selected area of the stent -23- in the deformed stent -21-, and in the stent in the reference configuration -20-, the corresponding region in the reference position, or reference region CU-R -22-, as well as the schematic depiction of the steps for determining the calculation of porosity in CU-D, determining CU-R from the area CU-D using Fs -24- (step E4), and determining the amount of metal occupied in CU-D once it is known in CU-R through Fp -25- (step E6).

In the method of the present invention, the representation of the stent and advantageously of the vessel in which it will be placed, is provided in the form of three-dimensional surfaces which can be obtained by means of any method known in the art, for example, by means of image segmentation of an angiographic image (Antiga, L. et al. "An image-based 5 modeling Framework for patient-specific computational hemodynamics." Medical and biological engineering and computing, 2008, 46(11), 1097-1112) and subsequent reconstruction of the surface (Lorensen, W. E. and Cline, H. E. "Marching Cubes: A high resolution 3D Surface construction algorithm." Computer Graphics, 1987, 21, 4). The three-dimensional surfaces of the structure of the stent and of the vessel can be depicted by means of polygon meshes, in which the resolution can be adjusted to obtain relevant information about the morphology thereof. As mentioned above, said techniques are known in the literature, and any of them can be used provided that it allows describing the morphology of the vessel in the region in which the stent will be placed and the morphology of the stent itself. It is also possible to apply it to a three-dimensional simulation of the positioning of the stent, provided that the initial and final positions in the vessel and the radii thereof are known.

With the method of the present invention not only is it possible to predict the porosity of a real or simulated stent once it is placed inside a vessel, but it is also possible to detect regions in which there may be a poor positioning of the stent in the walls of the vascular structure, such as in the case of blocking or complete or partial coverage of branched vessels.

With the use of the method of the present invention it is possible for the neurointerventional radiologist to plan the treatment and to know the porosity in each position of the stent before performing said treatment and, therefore, selecting the most suitable stent and the site where said stent should be placed.

Furthermore, according to the third aspect of the invention, the method of the present invention is implemented by means of a computer program which allows performing the determining of the final porosity of the stent more quickly and precisely.

A series of examples for determining the porosity or associated variables by applying the method proposed by the present invention are described below.

EXAMPLES

Example 1

Determining the relation of change in area covered by metal of the unit cell for a reference configuration. The selected configuration is one in which the stent is released without being subject to external stresses. In this position the unit cell can be defined as the entire stent for a single braiding angle. It is thereby possible to calculate the relation of change in area covered by metal with the total area from radially deforming the unit cell, the entire stent in this case, taking into account that the length of each wire is constant and that the amount of metal covering the surface is equal to the surface occupied by each wire (length times thickness) minus the amount of metal overlapping at the cross points.

The total area occupied by the stent can be calculated from the diameter $\phi$ and the length $L_{stent}$ of the stent.

$$A_{total} = \pi \cdot \phi \cdot L_{stent}$$

The amount of metal in the cross points is calculated based on the area occupied by the rhombus of FIG. 2 multiplied by the number of cross points of the stent; this relation can be expressed as:

$$A_{cross\ points} = \left(\frac{N_{wires}}{2}\right) \cdot \frac{L_{stent}}{L_c} \cdot \frac{l^2}{\sin(\alpha)}$$

$$L_c = L \cdot \cos\alpha/2$$

In this case $A_{total}$ represents the total area occupied by the surface of the stent, $A_{cross\ points}$ defines the area in the cross points between wires, $N_{wires}$ is the number of wires of the stent, $L_{stent}$ defines the length of the stent, l is the thickness of each wire, α is the angle between wires (i.e. twice the angle -3- indicated in FIG. 1) and $L_c$ is the longitudinal component of the distance between two consecutive cross points, element -4- in FIG. 3.

The following table shows the values of the area occupied by the surface of the stent with respect to the area of metal for a stent consisting of 48 wires with of diameter 4 mm, length of 16 mm, 0.04 mm of thickness in each wire and 1560 cross points and a distance between consecutive cross points along the wire of 0.3611, for different deformed positions of the stent, and therefore different angles α:

TABLE 1

| Total area [mm²] | Occupied area [mm²] |
|---|---|
| 20.7931 | 20.6476 |
| 75.3745 | 38.3293 |
| 138.5351 | 41.4003 |
| 182.9858 | 42.2906 |
| 202.7232 | 42.5608 |
| 195.0818 | 42.4627 |
| 161.0934 | 41.9136 |
| 105.3486 | 40.2458 |

Example 2

Determining the relation of change in the unit cell for a reference configuration. The rectangle occupied by the portion of wire between two consecutive cross points as shown in FIG. 3 is selected as a unit cell. The rotation and translational movement of this pattern generates a complete stent with a single braiding angle for the selected nominal position. The total area and the occupied area can be determined in a geometric manner from angle α/2, which is generated by the stent with the longitudinal direction, indicated as -3- in FIG. 3.

$$A_{total} = L^2 \cdot \frac{\sin(\alpha)}{2}$$

$$A_{occupied} = L^2 \cdot \frac{\sin(\alpha)}{2} - \left(L - \frac{l}{\sin(\alpha)}\right)^2 \cdot \frac{\sin(\alpha)}{2}$$

The following table shows the area occupied by the stent with respect to the total area for a stent consisting of 48 wires with diameter of 4 mm, length of 16 mm, wires with a thickness of 0.04 mm and 1560 cross points with a distance between cross points of 0.3611, for different deformed positions of the stent:

TABLE 2

| Total area [mm²] | Occupied Area [mm²] |
|---|---|
| 0.006664 | 0.006617 |
| 0.024158 | 0.012285 |

TABLE 2-continued

| Total area [mm²] | Occupied Area [mm²] |
|---|---|
| 0.039808 | 0.013134 |
| 0.055772 | 0.013509 |
| 0.064203 | 0.013632 |
| 0.063963 | 0.013629 |
| 0.055085 | 0.013497 |
| 0.038767 | 0.013099 |

Example 3

Calculation of porosity for a stent consisting of 48 wires with diameter of 4 mm, length of 16 mm, wire thickness of 0.04 mm, 1560 cross points and a homogenous porosity of 0.79 in its nominal position, i.e., in its reference configuration; it is deployed in a homogenous cylinder of 2 mm in diameter, in its deformed configuration.

The stent adopts a length of 21.84 mm when it is adapted inside the homogenous cylinder of 2 mm. The surface of the cylinder is divided into elements of 1 mm in the longitudinal direction and 1.26 mm on the perimeter. Therefore, the selected area element CU-D will have a surface of 1.26 mm². To calculate the surface element CU-R in the nominal configuration, i.e., in the reference configuration, the function $F_s$ is calculated. For this purpose, the transformation of area in the direction of the perimeter and in the longitudinal direction is calculated. In the direction of the perimeter, the transformation is determined by the difference of arcs for two radii of 2 mm and 4 mm, that is, an arc element of 1.26 mm on a radius of 2 mm corresponds to 2.52 mm of arc on a radius of 4 mm. The relation in the longitudinal direction is determined by the ratio between the lengths of the stent in its reference position and final position, 16 mm compared to 21.84 mm, so a length of 1 mm in the stent in its final position corresponds to 0.73 mm in its reference position, so the corresponding area in the nominal position corresponds to 2.52×0.73=1.83 mm². Therefore, once the porosity in the reference position is known, in this case 0.79, the occupied area in this position is (1−0.79)×1.26=0.38 mm².

The occupied area in the final position can be related with the reference area by calculating the variations in area of occupied metal with the variations in total area set forth in Tables 1 and 2. The total area of the stent in the deployed position and in the reference position can be calculated from its diameters and lengths. In this case, it corresponds to 202 mm² in the reference position and 138 mm² in the deployed position. Taking into account the occupied area values for each position, it is estimated that the variation in occupied area with the variation in total area (difference of the occupied area divided by the difference in total area) is in the order of −1/50, which in this case is calculated as (41.4−42.6)/(202−138)=0.01875, that is, when the variation in the selected total area is positive one (+1), the occupied area decreases 1/50 that amount. In the present case, the variation in the total area is 1.26−1.83=−0.62 mm², so the occupied area in the deployed position is 0.38−0.62*0.01875=0.368 mm², giving rise to a porosity of (1−0.368/1.26)=0.708.

Example 4

Calculation of porosity for a stent consisting of 48 wires with diameter of 4 mm, length of 16 mm, 0.04 mm of thickness in each wire and 1560 cross points and a homogenous porosity in its nominal (reference) position of 0.79 when it is deployed in a conical cylinder the diameter of which ranges from 4 mm to 1.5 mm.

The stent has a length of 19.7 mm when it is adapted inside the conical cylinder, which entails a change in length of 23%. The surface of the cylinder is divided into area elements of 1 mm in the longitudinal direction and of the total perimeter in the direction of the perimeter. The relation of change in length of the stent with the circumference can be experimentally estimated by deploying the stent on cylinders the diameters of which range from 4 mm to 1.5 mm, or analytically by taking into account that the stent is a spring-type structure having a known equation. The same calculations as those in the preceding example are performed in each 1 mm segment, taking into account that in this case the variations in occupied area with total area will be different for each segment of the cone of different radius being taken. The porosity in each segment is calculated again from the difference in area of the segment in the cone and of the equivalent section of segment over the nominal position, as well as in the corresponding occupied areas.

The calculation of porosity of one of these segments is described below. Firstly, it is assumed that each element of 1 mm in length has a constant diameter within that order of magnitude (the variation in the diameter in each segment is in the order of 0.13 mm). Therefore, the area of the stent is reconstructed by applying the Riemann sum concept. In addition, the variation in diameter from the start, 4 mm, until the end, 1.5 mm, is established through a linear equation, $\phi=4-(2.5/19.7)x$, where x is an integer taking values of 0 to 20. Finally, the change in length can be calculated by applying the equation of the helix. A stent with 48 wires means that in a perimeter in which the wires thereof cross, there are 24 cross points, which gives rise to 65 cross points in the longitudinal direction for a stent of 1560 cross points in total. Therefore, the number of turns of each wire along a length will be 65/48=1.35 turns per wire. The equation of the helix is expressed mathematically as:

$$L_{wire}^2 = L_{helix}^2 + (n \cdot \pi \cdot \phi)^2$$

where n is the number of turns and $L_{helix}$ is the longitudinal dimension of the helix, in the present case the length of the stent. Therefore, for each 1 mm segment and known diameter, it is possible to calculate what the length will be when it occupies its nominal diameter, 4 mm, by simply applying the changes in length determined by the equation of the helix, note that the length of the wire is constant for any diameter and length adopted by the stent and that it can be calculated from the nominal position of the length of helix and known diameters.

The first segment has a nominal radius of 4 mm, as there is no change in length associated with its diameter or with the morphology to which it is adapted, its porosity coincides with the nominal porosity.

The fourteenth segment of the stent in its deployed position in the conical cylinder has a diameter of 2.22 mm, which entails an area of 2.22*pi*1=6.97 mm$^2$ on a segment having 1 mm in length. For the purpose of calculating the length of the segment when the stent is in its nominal position, or nominal length, the equation of the helix is applied as follows.

Firstly, and given that the length of the wire is constant, the equation is balanced for two positions of known diameter, in this case for a diameter of 4 mm (nominal position) for which $L_{helix}$ is equal to the nominal length of the stent, i.e., 16 mm, and for a diameter of 2.22 mm (deployed position), for n=1.35. Therefore:

$$16^2 + (1.35 \cdot \pi \cdot 4)^2 = L_{deployed\ helix}^2 + (1.35 \cdot \pi \cdot 2.22)^2$$

where $L_{deployed\ helix}$ is the length of the helix corresponding to the deployed position for a diameter of 2.22 mm. Therefore:

$$L_{deployed\ helix} = (16^2 + (1.35 \cdot \pi \cdot 4)^2 - (1.35 \cdot \pi \cdot 2.22)^2)^{0.5} = (16^2 + (1.35 \cdot \pi)^2 \ast (4^2 - 2.22^2))^{0.5}$$

which gives a value for $L_{deployed\ helix}$ of 21.33 mm.

Considering that the length of the helix is reduced from 21.33 mm to 16 mm when it transitions from the deployed position to the nominal position, by applying a rule of 3 a segment of 1 mm in length in its deployed position will be reduced to a segment of nominal length equal to (21.33 mm*1 mm)/16 mm, i.e., of a value equal to 0.74 mm, so it corresponds to an area of 0.74*4*π=9.30 mm$^2$, which for a nominal porosity of 0.79 implies an occupied area of (1−0.79)*9.30=1.95 mm$^2$. Assuming that the corrective factor with the area is constant, equivalent to that calculated in Example 3, the occupied area in the fourteenth position will be 1.95+(6.97−9.30)/50=1.9 mm$^2$, which gives rise to a porosity of 1−(1.9/6.97)=0.72.

Figure 5:
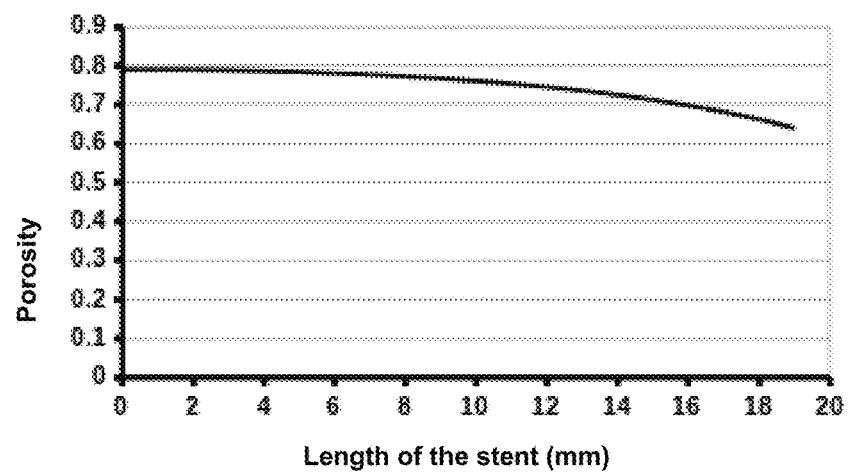
FIG. 5 is a graph showing the relation of change in porosity for each area element of the stent, according to Example 4, which will be described in the following section.

The relation of the change in porosity for each element of the stent inserted in the conical cylinder is shown in FIG. 5, where for the distance of 19 mm indicated in the graph the stent is adapted to the portion of the conical cylinder of 1.59 mm of diameter.

The present invention can also be applied to determining the porosity of a non-tubular shaped, braided or non-braided flexible porous structure, the surface of which is generated by elements of a known shape and placed in a given order, such as a WEB® system. When this type of porous structure is subjected to a deformation, it modifies both its shape and its porosity on the surface of the structure based on a new arrangement of the elements forming it.

A person skilled in the art will be able to introduce changes and modifications to the described embodiments without departing from the scope of the invention as it is defined in the attached claims.

The invention claimed is:

1. A method for determining the porosity of a flexible porous structure when it is subjected to deformation, comprising performing the following steps by means of processing representative data of said flexible porous structure:
    a) generating a first function ($F_s$) defining how at least one part of the flexible porous structure, given its coordinates, changes shape when it is subjected to one or more geometric deformations, wherein said change of the shape is determined in two directions, one in a cross-section of the flexible porous structure ($F_{s1}$) and the other in a longitudinal direction ($F_{s2}$);
    b) generating a second function ($F_p$) defining how a covered surface, and/or a variable associated with same, for at least one part of the flexible porous structure, changes when it is subjected to one or more changes in shape, said second function ($F_p$) being directly linked with porosity of the flexible porous structure;
    c) obtaining, by means of said first function ($F_s$), reference porosity values of at least one reference region (CU-R) of the flexible porous structure in a reference configuration; and
    d) calculating the porosity of at least one deformed region (CU-D) of the flexible porous structure corresponding with said reference region (CU-R) but for a deformed configuration different from said reference configuration, from said obtained reference porosity values of the reference region (CU-R) and from at least said second function ($F_p$).

2. The method according to claim 1, wherein said data makes up respective three-dimensional representations of the flexible porous structure for each of the configurations: the reference configuration and the deformed configuration, wherein the data making up said three-dimensional representations are obtained by means of simulation or are obtained directly on a real flexible porous structure placed covering an outer surface of a solid or hollow element, or an inner surface demarcating a hollow region of an element.

3. The method according to claim 1, wherein said variable associated with porosity is relative to the occupancy of the material forming the flexible porous structure.

4. The method according to claim 1, wherein said variable associated with porosity is relative to the degree of interstitial space, or free space of the material forming the flexible porous structure.

5. The method according to claim 1, further comprising:
x1) selecting, before said step c), at least said deformed region (CU-D) of the flexible porous structure in said deformed configuration; and
x2) calculating, after said step c), the shape of at least said reference region (CU-R) of the flexible porous structure using said first function ($F_s$), using the coordinates corresponding to the deformed region (CU-D),
wherein said second function ($F_p$) generated in step b) defines how the occupancy of the material forming the flexible porous structure changes for at least said part of the flexible porous structure;
after said step x2) and prior to the calculation of porosity of the flexible porous structure in the deformed region (CU-D) of said step d), the method comprises calculating the occupancy of the material forming the flexible porous structure for at least said reference region (CU-R), from said reference porosity values; and
said step d) comprises:
d1) calculating the occupancy of the material forming the flexible porous structure for at least said deformed region (CU-D) using the second function ($F_p$) and the calculated occupancy of the reference region (CU-R); and
d2) calculating the porosity in the deformed region (CU-D) from said occupancy of same calculated in d1) and from its total dimension.

6. The method according to claim 5, wherein said step d2) comprises calculating the degree of interstitial space, or free space of the material forming the flexible porous structure, from said occupancy, and carrying out said calculation of porosity from said degree of interstitial space by calculating the quotient between interstitial space and total space of the deformed region (CU-D).

7. The method according to claim 1, wherein both said parts of the flexible porous structure and said deformed region (CU-D) and reference region (CU-R) are area elements on a perimetral surface of the flexible porous structure.

8. The method according to claim 1, wherein said flexible porous structure is tubular.

9. The method according to claim 8, wherein:
said first function ($F_s$) defines how a perimetral surface of the flexible porous structure changes shape when it is subjected to one or more geometric deformations; and
said second function ($F_p$) defines how the covered surface and/or said variable associated with same for the perimetral surface of the flexible porous structure, changes when it is subjected to one or more changes in shape.

10. The method according to claim 5, wherein:
the deformed regions (CU-D) are not superimposed on one another; or
the deformed regions (CU-D) completely occupy a perimetral surface of the flexible porous structure, where the method comprises dividing said perimetral surface into said deformed regions (CU-D) prior to step x1).

11. The method according to claim 10, further comprising processing the several porosity values obtained in the corresponding steps d) to perform at least one of the following actions:
determining the spatial distribution of porosity throughout the flexible porous structure;
obtaining a porosity value combining at least several of said porosity values for a zone of the flexible porous structure that includes several deformed regions (CU-D); and
visually representing on a three-dimensional model of the flexible porous structure the spatial distribution of porosity for individual deformed regions (CU-D) and/or groups of deformed regions (CU-D),
Wherein the reference configuration corresponds to a situation in which the flexible porous structure is released into a medium in which it is not subject to external stresses deforming it, or wherein the reference configuration corresponds to a situation in which the flexible porous structure is deformed but with a reference deformation that is different from that of said deformed configuration.

12. The method according to claim 11, wherein said reference deformation is a deformation that keeps the flexible porous tubular structure straight and with a uniform radius along its entire length, wherein said flexible porous structure is tubular.

13. The method according to claim 1, wherein the flexible porous structure adopts, for said deformed configuration, a heterogeneous radius and a heterogeneous three-dimensional morphology, where said heterogeneous three-dimensional morphology includes at least one curvature and/or at least one twist.

14. The method according to claim 2, further comprising carrying out said calculation of porosity for several deformed spatial configurations, with different deformations, corresponding to several respective positions adopted by the flexible porous structure in said simulation or in relation to said element.

15. The method according to claim 1, wherein said flexible porous structure is a stent.

16. The method according to claim 1, wherein in said deformed configuration the flexible porous structure adopts a conical shape.

17. The method according to claim 1, wherein said reference porosity values of said reference region (CU-R) are known and are recorded in a memory, where the method performs said obtaining of said porosity values of said reference region (CU-R) by accessing same in said memory.

18. A system for determining the porosity of a flexible porous structure when it is subjected to deformation, comprising a data processing unit with access to reference porosity values of at least one reference region (CU-R) of the flexible porous structure in a reference configuration, and which implement an algorithm for processing representative data of said flexible porous structure for the calculation of porosity by:
a) generating a first function ($F_s$) defining how at least one part of the flexible porous structure, given its coordinates, changes shape when it is subjected to one or more geometric deformations, wherein said change of the shape is determined in two directions, one in the cross-section of the flexible porous structure ($F_{s1}$) and the other in the longitudinal direction ($F_{s2}$);

b) generating a second function ($F_p$) defining how a covered surface, and/or a variable associated with same, for at least one part of the flexible porous structure, changes when it is subjected to one or more changes in shape, said second function ($F_p$) being directly linked with porosity of the flexible porous structure;

c) obtaining, by means of said first function ($F_s$), reference porosity values of at least one reference region (CU-R) of the flexible porous structure in a reference configuration; and d) calculating the porosity of at least one deformed region (CU-D) of the flexible porous structure corresponding with said reference region (CU-R) but for a deformed configuration different from said reference configuration, from said obtained reference porosity values of the reference region (CU-R) and from at least said second function ($F_p$).

19. The system according to claim 18, further comprising:
a computing unit including said processing unit;
a display unit configured for, under the control of said computing unit, showing a three-dimensional representation of the flexible porous structure for the deformed configuration with the spatial distribution of porosity calculated for individual deformed regions (CU-D) and/or groups of deformed regions (CU-D),
wherein the computing unit being further configured for carrying out said calculation of porosity for several deformed configurations, with different deformations, corresponding to several respective positions adopted by the flexible porous structure, and for controlling the display unit so that they show a three-dimensional representation of the flexible porous structure for said deformed configurations with their respective spatial distributions of porosity for individual deformed regions (CU-D) and/or groups of deformed regions (CU-D).

20. A computer program product including code instructions which when they are run in a computer implement a method for determining the porosity of a flexible porous structure when it is subjected to deformation by performing the following steps:

a) generating a first function ($F_s$) defining how at least one part of the flexible porous structure, given its coordinates, changes shape when it is subjected to one or more geometric deformations, wherein said change of the shape is determined in two directions, one in the cross-section of the flexible porous structure ($F_{s1}$) and the other in the longitudinal direction ($F_{s2}$);

b) generating a second function ($F_p$) defining how a covered surface, and/or a variable associated with same, for at least one part of the flexible porous structure, changes when it is subjected to one or more changes in shape, said second function ($F_p$) being directly linked with porosity of the flexible porous structure;

c) obtaining, by means of said first function ($F_s$), reference porosity values of at least one reference region (CU-R) of the flexible porous structure in a reference configuration; and d) calculating the porosity of at least one deformed region (CU-D) of the flexible porous structure corresponding with said reference region (CU-R) but for a deformed configuration different from said reference configuration, from said obtained reference porosity values of the reference region (CU-R) and from at least said second function ($F_p$).

* * * * *